United States Patent [19]

Kurdjumova et al.

[11] Patent Number: 4,933,332
[45] Date of Patent: * Jun. 12, 1990

[54] 11-DESOXY-17-α-HYDROXYCORTICOSTERONE DERIVATIVES

[76] Inventors: Kira N. Kurdjumova, Volokolamskoe shosse, 80, kv. 34; Elizaveta N. Shkodinskaya, Kashirskoe shosse, 28, korpus 1, kv. 40; Ljudmila P. Sushinina, Matveevskaya ulitsa, 10, korpus 4, kv. 124; Valentina P. Yaguzhinskaya, ulitsa Akademika Millionschikova, 16, kv. 48; Nina D. Lagova, Kashirskoe shosse, 60, korpus 2, kv. 25; Zoya P. Sofiina, Kashirskoe shosse, 28, korpus 1, kv. 9; Irina M. Valueva, Kashirskoe shosse, 28, korpus 2, kv. 55; Petr V. Lopatin, ulitsa Akademika Millionschikova, 16, kv. 22; Margarita A. Krasnova, prospekt Mira, 99, kv. 277; Anatoly B. Syrkin, ulitsa Gasheka, 12, kv. 65; Ljudmila M. Mikhailova, B. Rogozhsky pereulok, 10, korpus 2, kv. 79, all of Moscow, U.S.S.R.

[ * ] Notice: The portion of the term of this patent subsequent to Mar. 7, 2006 has been disclaimed.

[21] Appl. No.: 252,259

[22] Filed: Sep. 30, 1988

Related U.S. Application Data

[63] Continuation of Ser. No. 852,459, Mar. 21, 1986, Pat. No. 4,810,701.

[51] Int. Cl.$^5$ .......................... A61K 31/56; C07J 1/00
[52] U.S. Cl. .................................... 514/181; 552/595
[58] Field of Search .................... 260/397.47; 514/181

[56]     References Cited
U.S. PATENT DOCUMENTS 4,810,701 3/1989 Kurdjumova et al. ........ 260/397.47

OTHER PUBLICATIONS

Effects of Steroidal Alkylating Agents; Wall et al.; vol. 12, pp. 810-818.

Primary Examiner—Joseph A. Lipovsky
Attorney, Agent, or Firm—Burgess, Ryan and Wayne

[57]     ABSTRACT

11-Desoxy-17α-hydroxycorticosterone derivatives of the general formula:

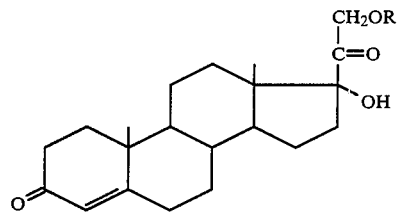

wherein R is —OC(CH$_2$)$_n$C$_6$H$_4$N(CH$_2$CH$_2$Cl)$_2$, n=1,3.

4 Claims, No Drawings

11-DESOXY-17-α-HYDROXYCORTICOSTERONE DERIVATIVES

This is a continuation of application Ser. No. 852,459, filed Mar. 21, 1986, now U.S. Pat. No. 4,810,701.

FIELD OF THE INVENTION

The present invention relates to the bio-organic chemistry and, more particularly, to novel 11-desoxy-17α-hydroxycorticosterone derivatives (hormonocytostatics) exhibiting both antitumor and hormonal activity and useful in medicine as cancer treatment agents and immunodepressants.

BACKGROUND OF THE INVENTION

Known in the art are esters of corticoids, intermediate products of their biosynthesis and cytotoxic acids of different structure.

They can be exemplified by esters of pregnenolone and p-di-(2-chloroethyl)aminophenylacetic acid (chlorophenacyl):

3β-hydroxy-5-pregnen-20-one-3α-p-di(2-chloroethyl)aminophenylacetate

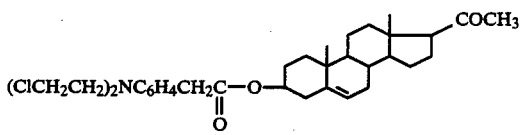

and desoxycorticosterone and chlorophenacyl-21-hydroxy-4-pregnen-3,20-dione-21-[p-di(2-chloroethyl)aminophenylacetate]:

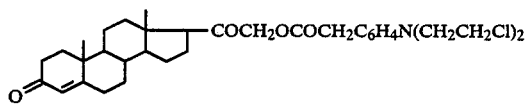

The antitumor properties of these compounds have been studied but insufficiently. There has been established their antitumor activity against Walker carcinosarcoma W-256, chronic leukemia of rats and certain tumors originating from hormone-depending tissues-cervical carcinoma RShM-5, mammary carcinoma R-13726. However, these compounds have not revealed any activity in respect of lymphoid leukemia L 1210 (cf. Z. P. Sof'ina, N. D. Lagova, I. M. Valueva, Z. V. Kuz'mina, E. N. Shkodinskaya, A. M. Khaletsky. Proceedings of I All-Union Conference on Chemiotherapy of Malignant Tumors, Riga, 1968, p. 441–443; M. Wall, G. Abernethy, F. Carrol, D. Taylor, J. Med. Chem., 1969, 12, No. 5, pp. 810–818; N. D. Lagova. Experimental Oncology 1982, vol. 4, No. 5, p. 38–42).

Known are esters of corticoids, more particularly esters of hydrocortisone and β-chloroethylcarbamic acid; 9αF,11β,16α, 17α,26-tetraoxypregna-1,4-diene-3,20-dione-21-[bis-(2-chloroethyl)carbamate], 16,17-acetonide

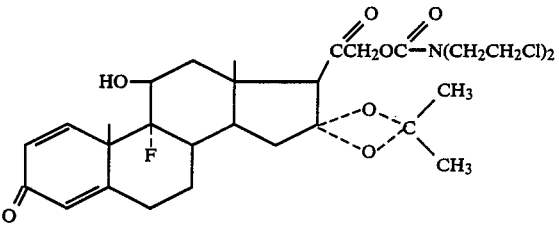

and esters of triamcinolone-acetonide and β-chloroethylcarbamic acid: 11β,17α,21-trihydroxy-pregnene-4-3,20-dione-21-[bis(2-chloroethyl)carbamate]:

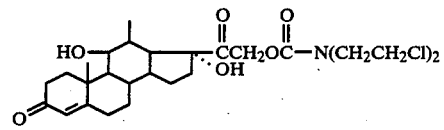

The compounds are biologically active. They inhibit growth of cultures of mice fibroblasts L-929 and react with cell receptors. However, these biological effects are reversible (cf. A. Masry, V. Braun, C. Nielsen, W. Pratt, J. Med. Chem., 1977, vol. 20, No. 9, pp. 1134–1139).

Known in the art is an ester of a synthetic corticoid-prednisolone and p-di-(2-chloroethyl)aminophenyl-butyric acid (chlorambucyl): pregna-1,4-diene-3,20-dione, 11β17,21-trihydroxy-21-[p-di(2-chloroethyl)aminophenylbutyrate] of the formula:

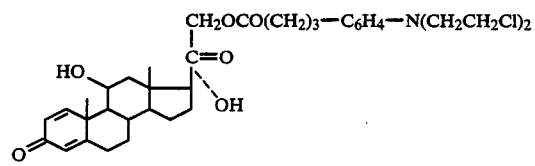

which was give the tradename "Prednimustine" (D. Alftchew, I. Rush. Ann. Chir, Gynaecol. Fenw., 1969, vol. 58, p. 234; J. Kaufmann, G. Hunjura, A. Mittelmann, C. Arengsta, G. Murphy, Cancer. Treat. Rep. 1976, vol. 60, No. 3, pp. 277–279).

The preparation "Prednimustine" is useful in oncological clinic for the treatment of systemic blood diseases and, to a lesser extent—breast cancer. Side effects of "Prednimustine" are associated mainly with hematotoxicity.

DISCLOSURE OF THE INVENTION

The present invention is directed to the provision of novel 11-desoxy-17α-oxycorticosterone derivatives exhibiting a wide range of an antitumoral effect and hormonal activity.

The 11-desoxy-17α-oxycorticosterone derivatives are novel and hitherto unknown from the literature.

The object of the present invention is accomplished by providing the derivatives of 11-desoxy-17α-hydroxycorticosterone comprise compounds of the general formula:

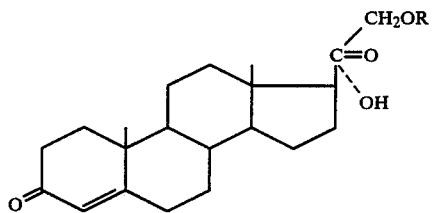

wherein R is —CO(CH₂)ₙC₆H₄N(CH₂CH₂Cl)₂; n=1, 3.

In the compounds according to the present invention as the steroid use is made of 11-desoxy-17α-oxycorticosterone which is a hormone-mediator in the biosynthesis of mineralo- and glucocorticoids and is also capable of metabolizing according to the estrogen type.

The compounds according to the present invention comprise esters of 11-desoxy-17α-hydroxycorticosterone and p-di(2-chloroethyl)aminophenylalkane acids.

Examples of the compounds according to the present invention are 11-desoxy-17α-hydroxy-21-[p-di(2-chloroethyl)aminophenylacetate]corticosterone and 11-desoxy-17α-hydroxy-21-[p-di-(2-chloroethyl)aminophenylbutyrate] corticosterone.

The compounds according to the present invention comprise fine crystals of a white or white with a yellowish tint colour, substantially insoluble in water, soluble in organic solvents (chloroform, benzene, ethylacetate), non-hygroscopic, acquire a yellow colour upon a long-time storage in the light. The compounds are stable for a long time when stored in darkness at a temperature within the range of from 5° to 0° C.

It is advisable to make use of a derivative of 11-desoxy-17α-hydroxycorticosterone of the formula:

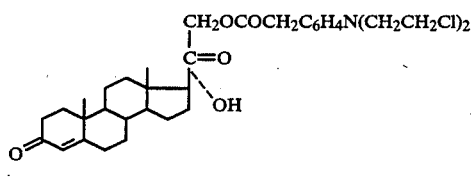

BEST MODE FOR CARRYING OUT THE INVENTION

The compounds according to the present invention exhibit a high antitumor activity which has been demonstrated on regrafted leukoses. The antitumor effect is expressed in an extended lifespan of animals and recovery of some of them.

The compounds according to the present invention have the advantage residing in their low toxicity as compared to constituting them highly-toxic alkylation agents, namely chlorophenacyl and chlorambucyl. Thus, the equimolar dose of chlorophenacyl in chlorambucyl contained in therapeutic doses of the compounds according to the present invention exceeds their own therapeutic dose by 5–10 times.

For the study of the antitumor activity of the compounds according to the present invention use was made of regrafted hemoblastoses, grafted solid tumors, induced and spontaneous tumors of mice and rats. The following models were used: L 1210, P-388, hemocytoblastosis La, MOPC-406, viral lympholeukosis Mazurenko LMC-1, Ca-755, mammary carcinoma metastasizing into lungs KML, alveolar mammary cancer RMK-1, small intenstine adenocarcinoma AKATON, large intestine adenocarcinoma AKATOL, Lewis lung carcinoma LL, lung adenocarcinoma RL-67, hepatomae G-22c, G-60, G-61, sarcomae S-37 and S-180, DMBA (dimethylbenzanthracene)-induced and spontaneous mammary tumors, and DMN (dimethylhydrazine)-induced tumors of the large intestine.

The studies were carried out on line mice and their first-generation hybrids, as well as on mongrel mice and rats.

The compounds were administered to the animals hypodermally in kernel oil. The administration conditions are shown in tables hereinbelow. For the purpose of comparison, a known hormonocytostatic estracyte (estra-1,3,5-(10)treine-3,17β-diol-3N-[bis-(2-chloroethyl)carbamate-17-sodium phosphate] was used which was administered hypodermally in a solution of a 0.9% NaCl, chlorphenacyl and chloroambucyl which were administered intraperitoneally in a 10% solution of ethanol, sarcolysine (β-[p-di(2-chloroethyl)aminophenyl]-α-alanine hydrochloride)—intraperitoneally in a 0.9% solution of NaCl, prednisolone (pregnadiene-1,4-triol-11β,17α,21-dione-3,20)—per os in a starch size.

Criteria of the antitumor activity of the compounds according to the present invention are: extension of the lifespan of the animals (ELA, %) and tumor growth inhibition (TGI, %).

$$ELA, \% = \frac{C-T}{C} \times 100, \text{ wherein:}$$

T—average lifespan of the treated animals;
C—average lifespan of the control animals.

$$TGI, \% = \frac{K-O}{K} \times 100, \text{ wherein:}$$

O—average tumor volume in the group of treated animals;
K—average tumor volume in the group of control animals.

In the case of using spontaneous or induced tumors, by means of carcinogenic substances, the criteria of the antitumor effect are: TGI, % or decrease in the tumor size, %, as compared to its initial value. The treatment of spontaneous and induced tumors was initiated after achieving, by these tumors, of a particular size excluding the possibility of a spontaneous regression.

The data on the antileukosis activity of the compounds according to the present invention are given in Table 1.

TABLE 1

Antitumor effect of the compounds according to the present invention on grafted hemoblastoses

| No. | Compound | Range of effective doses (mg/kg), time interval (h) × x number of administrations | L 1210 1-5 | L 1210 2-6 | P-388 1-5 | P-388 2-6 | MOPG-406 1-5 | MOPG-406 2-6 | La 1-5 | Viral leukosis Mazurenko LMC-1 2-6 |
|---|---|---|---|---|---|---|---|---|---|---|
| 1 | 2 | 3 | 4 | 5 | 6 | 7 | 8 | 9 | 10 | 11 |
| 1. | 11-Desoxy-17α-hydroxy-21-[p-di(2-chloroethyl)-aminophenyl-acetate] corticosterone | 10–25/24 × 5 | 31 | | 81 | | 76 | | 105 | 344 (33% of cure) |
| 2. | 11-Desoxy-17α-hydroxy-21-[p-di(2-chloroethyl)-aminophenyl-butyrate] corticosterone | 15–35/24 × 5 | | 20 | | 82 | | 70 | 18 | |
| 3. | Chlorophenacyl | 1.5–3/24 × 5 | | 15 | | 87 | | 41 | 46 | 9 |
| 4. | Chlorambucyl | 2.5–4/24 × 5 | | 7 | | 49 | | 35 | | |
| 5. | 11-Desoxy-17α-hydroxycorticosterone | 7–15/24 × 5 | | 6 | | −7 | | 0 | | 17 |
| 6. | 11-Desoxy-17α-hydroxy-corticosterone + chlorphenacyl | 7/24 × 5 + 1.5/24 × 5 | | | | | | 46 | | |
| 7. | 11-Desoxy-17α-hydroxy-corticosterone + chlorambucyl | 7–15/24 × 5 + 2.5–4/24 × 5 | | | | | | 57 | 35 | |

TABLE 2

Antitumor effect of 11-desoxy-17α-hydroxy-21-[-p-di(2-chloroethyl)aminophenylacetate]chloroethyl)aminophenylacetate] corticosterone on grafted solid tumors

| No. | Compound | Range of effective doses, (mg/kg), interval (h) × number of administrations | Ca-755 2 | Ca-755 2-6 | S-37 2 | S-37 2-6 | S-180 2-6 | AKATOL 2-6 | LL 2 | LL 2-6 | G-22c 2-6 | G-60 6-10 | G-61 7-11 | RMK-1 3-7 |
|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 |
| 1. | 11-Desoxy-17α-hydroxy-21-[p-di(2-chloroethyl)-aminophenyl-acetate] corticosterone | 45 × 1<br>10–25/24 × 5 | 94 | 99 | 99 | 99 | 93<br>92 | 98 | 90 | 81 | 80 | 99 | 89 | 59 |
| 2. | Chlorophenacyl | 1.5–2/24 × 5 | | 87 | | 94 | 56 | 46 | | 16 | 29 | 86 | 53 | 27 |
| 3. | 11-Desoxy-17α-hydroxycorticosterone | 7–10/24 × 5 | | +105 | | 29 | | +41 | | 28 | 3 | 38 | 37 | +4 |
| 4. | Prednisolone | 4–10/24 × 5 | | 70 | | 44 | | 67 | | 30 | | | 44 | |
| 5. | Sarcolysine | 2–3/24 × 5 | | 83 | | 95 | 76 | 56 | | 58 | | 90 | 87 | +86 |
| 6. | Estracyte | 100/24 × 5 | | +6 | | 85 | +23 | | | 29 | | | | |

NOTE:
Sign "+" means stimulation of tumor growth.

It is seen from Table 1 that both compounds according to the present invention exhibit an antileukosis activity which is manifested in an extended lifespan of the animals with hemoblastoses L 1210, P-388, MORC-406, La and LMC-1.

The antitumor effect of the compounds according to the present invention is superior to that of the alkylation agents incorporated in their molecule (chlorophenacyl and chlorambucyl). It is also superior to the combined effect of chlorophenacyl and chlorambucyl with 11-desoxy-17α-hydroxycorticosterone.

Table 2 shown the data of the antitumor effect of 11-desoxy-17α-hydroxy-21-[p-di(2-chloroethyl)aminophenylacetate] corticosterone in respect of solid tumors.

It is seen from Table 2 that the compound according to the present invention has a high antitumor activity and a wide spectrum of the antitumor effect. It inhibits growth of substantially all tumors by 80–99%. This compound is active in respect of animals with tumors insensitive to the components constituting its molecule, other corticoids and the hormonocytostatic-estracyte. 11-Desoxy-17α-hydroxy-21-[p-di(2-chloroethyl)aminophenylacetate] corticosterone is considerably superior, as regards its activity on numerous models, over the known alkylating preparation sarcolysine.

11-Desoxy-17α-hydroxy-21-[p-di(2-chloroethyl)amino-phenylacetate] corticosterone causes a long-time antitumoral effect and inhibits growth of tumors for 1 month and longer after completion of the treatment course which results in an extension of the lifespan of the animals by 27–73% as compared to the control (Table 3).

TABLE 3

Duration of the antitumor effect of 11-desoxy-17α-hydroxy-21-[p-di-(2-chloroethyl)aminophenylactate] corticosterone

| No. | Models of tumors | Dose, (mg/kg) interval (h) × number of administrations | Days of treatment after grafting | Tumor growth inhibition, % days of experiment | | | Extension of the lifespan, % |
|---|---|---|---|---|---|---|---|
| | | | | 15 | 22 | 29 | |
| 1 | 2 | 3 | 4 | 5 | 6 | 7 | 8 |
| 1. | Lung adenocarcinoma RL-67 | 45 × 1 | 2 | 81 | 82 | 80 | 27 |
| 2. | Breast carcinoma metastasizing into lungs KML | " | 10 | 80 | 53 | 61 | 57 |
| 3. | Sarcoma S-37 | " | 2 | 99 | 94 | 91 | 42 (28% of recovery) |
| 4. | Hepatoma G-22c | 15/24 × 5 | 6–10 | 80 | 68 | 57 | 65 |
| 5. | Lewis epidermoidal lung carcinoma LL | " | 2–6 | 76 | 56 | 39 | 38 |
| 6. | Mammary adenocarcinoma Ca-755 | " | 2–6 | 92 | 73 | 82 | 73 |
| 7. | Small intestine adenocarcinoma AKATON | " | 2–6 | 66 | 55 | 46 | 46 |

11-Desoxy-17α-hydroxy-21-[p-di(2-chloroethyl)aminophenylacetate] corticosterone causes reduction in size of induced and spontaneous tumors in breasts in rats and mice as compared to the size thereof prior to the treatment; it also reveals activity in repeated treatment courses (Table 4) which points to the absence of thereapeutical adaptation to this compound.

The hormonal effect of 11-desoxy-17α-hydroxy-21-[p-di-(2-chloroethyl)aminophenylacetate] corticosterone is associated with exhibition of a glucocorticoidal activity thereby. Under specific administration conditions the compound extends the lifespan of 25-days adrenalectomized rat youngsters (biological test for the glucocorticoidal activity) likewise 11-desoxy-17α-hydroxycorticosterone incorporated therein (by 113 and 115% respectively). A specific feature of the hormonal effect of the compound according to the present invention resides in its ability of causing a short-time estral response in animals. The corticoidal activity of the compound is also revealed in the study of the biochemical mechanism of its antitumoral effect. The compound interacts with cytoplasmatic receptors of glucocorticoids and inhibits combining of [$^3$H]-dexamethazone therewith. The high affinity of the compound to receptors of glucocorticoids is demonstrated by a small value of the dissociation constant of its receptor complex which is equal to $9.5 \times 10^{-8}$M.

11-Desoxy-17α-hydroxy-21-[p-di(2-chloroethyl)aminophenylacetate] corticosterone reacts with receptors of glucocorticoids in grafted tumors of animals, namely: RL-67, G-60, G-61, G-22c, Ca-755, S-37, AKATOL, AKATON on which it exhibits a high antitumoral activity. The inhibition, thereby, of a specific combining of [$^3$H]-dexamethazone in tumors of animals reaches 70–100%. 11-Desoxy-17-α-hydroxy-21-[p-di(2-chloroethyl)aminophenylacetate] corticosterone also reacts with cytoplasmatic receptors of glucocorticoids in tumors in human beings. The inhibition of the specific combining of [$^3$H]-dexamethazone thereby in the case of human lung cancer is 83%, in the case of breast cancer—53%, stomach cancer—69% and kidney cancer—84%.

11-Desoxy-17α-hydroxy-21-[p-di(2-chloroethyl)aminophenylacetate] corticosterone penetrates into the cell nucleus and interacts with acceptor regions of chromatin of both tumoral and normal cells (kidney tumor PA of rats, line Wistar, normal kidney).

As regards the manifestation of alkylation properties, 11-desoxy-17α-hydroxy-21-[p-di(2-chloroethyl)aminophenylacetate] corticosterone differs from chlorophenacyl incorporated therein, especially in its effect on the tumor. The alkylation power was evaluated through the dynamics of appearance of cross-linking and ruptures in molecules of desoxyribonucleic acid (DNA) of both tumoral (sarcoma S-37) and normal (spleen) cells using methods of sedimentation at the density gradient of alkaline saccharose.

TABLE 4

Effect of 11-desoxy-17α-hydroxy-21-[p-di(2-chloroethyl)-aminophenylacetate] corticosterone on spontaneous and induced breast tumors in repeated treatment courses

| No. | Tumors | Group | Dose (mg/kg), interval (h) × number of administrations per course | Decrease or increase (+) of the tumor size, % of the initial one weeks of the experiment | | | | | | | | Increased lifespan, % |
|---|---|---|---|---|---|---|---|---|---|---|---|---|
| | | | | 1 | 2 | 3 | 4 | 5 | 6 | 7 | 8 | |
| 1 | 2 | 3 | 4 | 5 | 6 | 7 | 8 | 9 | 10 | 11 | 12 | 13 |
| 1. | Spontaneous mammary tumors of mice | Control | | +25 | +42 | +89 | +155 | +230 | +330 | +505 | +412 | |
| 2. | | 11-Desoxy-17α-hydroxy-21-[p-di(2-chloroethyl)aminophenylacetate] corticosterone | 15/24 × 5 (2 courses with the interval of 3 weeks) | 23 | 37 | +7 | 64 | 20 | 50 | 25 | 16 | 11 |
| 3. | DMBA-induced mammary tumors of rats | Control | | +86 | +160 | +215 | +258 | +269 | +355 | +400 | +409 | |
| 4. | | 11-Desoxy-17α-hydroxy-21-[p-di(2-chloroethyl)aminophenylacetate] | 15/24 × 5 (2 course with the interval of 5 weeks) | 33 | 32 | 11 | 24 | +26 | 23 | +3 | 13 | 18 |

TABLE 4-continued

Effect of 11-desoxy-17α-hydroxy-21-[p-di(2-chloroethyl)-aminophenylacetate] corticosterone on spontaneous and induced breast tumors in repeated treatment courses

| No. | Tumors | Group | Dose (mg/kg), interval (h) × number of administrations per course | Decrease or increase (+) of the tumor size, % of the initial one weeks of the experiment | | | | | | | | Increased life-span, % |
|---|---|---|---|---|---|---|---|---|---|---|---|---|
| 1 | 2 | 3 | 4 | 1 | 2 | 3 | 4 | 5 | 6 | 7 | 8 | |
|   |   |   |   | 5 | 6 | 7 | 8 | 9 | 10 | 11 | 12 | 13 |
|   |   | corticosterone |   |   |   |   |   |   |   |   |   |   |

In respect of the number and duration of retention of cross-linking in DNA molecules of cells of S-37, 11-desoxy-17α-hydroxy-21-[p-di(2-chloroethyl)aminophenylacetate] corticosterone is superior to chlorophenacyl incorporated therein. In a normal tissue regeneration of DNA injured by 11-desoxy-17α-hydroxy-21-[p-di(2-chloroethyl)aminophenylacetate] corticosterone starts earlier than in the tumor tissue which points to the fact that the compound reveals selectivity of the injuring effect on DNA of tumor cells.

The toxicological study of the compounds according to the present invention has been carried out on mice. It has been shown that the gap between toxic and tolerated doses is sufficiently high. 11-desoxy-17α-hydroxy-21-[p-di(2-chloroethyl)aminophenylacetate] corticosterone has toxicity which is 3 times lower than that of chlorophenacyl incorporated therein. The MTD and $LD_{50}$ values at a single administration of the compound are equal to 44 and 80 mg/kg respectively, whereas for chlorophenacyl they are equal to 15 and 24 mg/kg respectively. 11-desoxy-17α-hydroxy-21-[p-di(2-chloroethyl)aminophenylbutyrate] corticosterone has even lower toxicity. Its MTD upon a single-time administration is equal to 350 mg/kg, whereas for chlorambucyl it is equal to 25 mg/kg.

The toxicological study has shown that the use of 11-desoxy-17α-hydroxy-21-[p-di(2-chloroethyl)aminophenylacetate] corticosterone can be limited by the gastroenteral and neurotoxicity (diarrhea, vomition, convulsions) the degree of which depends on the dose. Hematotoxicity usually limiting administration of preparations with alkylating properties and of the preparation "Prednimustine" does not restrict the administration of 11-desoxy-17α-hydroxy-21-[p-di-(2-chloroethyl)aminophenylacetate] corticosterone.

The compounds according to the present invention exhibit an immunodepressant effect. Characteristics of humoral immunity after introduction of the compounds in single a maximum tolerable dose (MTD) are essentially lowered as compared to the control and remain low over a period of up to 1.5 months. It should be noted that the immunodepressant effect of the compounds is revealed in respect of T-suppressors and in doses lower than a single therapeutical dose.

The method for the preparation of the compounds according to the present invention is simple and can be performed in the following manner.

The synthesis of the compounds according to the present invention can be represented by the following scheme:

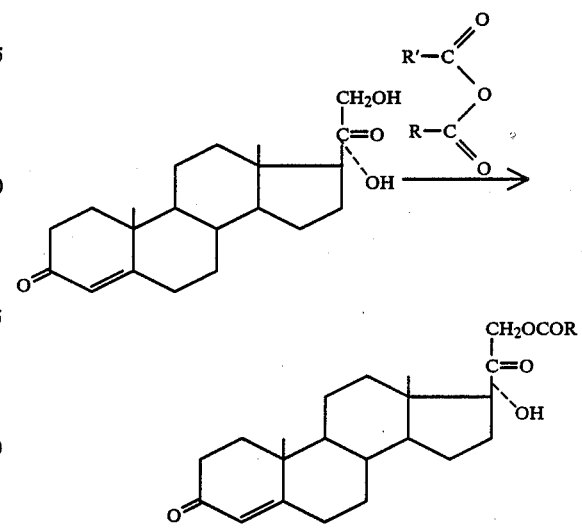

wherein R' is $-CH_2CH(CH_3)_2$.
R is $-(CH_2)_nC_6H_4N(CH_2CH_2Cl)_2$; n=1, 3.

The compounds are prepared by the method of mixed anhydrides which, as it has been experimentally demonstrated, provides better results as compared to the anhydride and chloride methods. The method of mixed anhydrides is based on acylation of a steroidal hydroxycompound with a mixed anhydride of a cytotoxic derivative of a phenylalkane acid and isovaleric acid.

The preparation of a mixed anhydride is effected in a medium of an aprotic solvent such as benzene at the temperature of +5° C. in the presence of a molar amount of triethylamine. The mixed anhydride is entered into the reaction of acylation of the hydroxy group in the side chain of 11-desoxy-17α-hydroxycorticosterone.

The process according to the present invention can be readily implemented on a commercial scale, since it is simple and necessitates no high power consumption.

All the reagents employed in the process are known compounds and can be readily available.

For a better understanding of the present invention some specific examples are given hereinbelow.

EXAMPLE 1

Preparation of 11-desoxy-17α-hydroxy-21-[p-di(2-chloroethyl)-aminophenylacetate] corticosterone (I)

15.9 g (0.057 g-mol) of chlorophenacyl are dissolved in dry benzene, added with 8.0 ml (5.83 g, 0.57 g-mol) of triethylamine and 7.8 ml (7.71 g, 0.064 g-mol) of isovaleric acid chloride at the temperature of +5° C.

The reaction mixture is stirred for one hour at the temperature of 5° C., then added with 200 ml of dry acetonitrile and 20.0 g of 11-desoxy-17α-hydroxycroticosterone (0.057 g-mol). The reaction mass is heated for 4 hours at the temperature of 80° C., added with 100 ml of benzene, whereafter the formed organic layer is washed in succession with water, a solution of sodium bicarbonate and again with water.

The organic layer is separated and dried with anhydrous sodium sulphate. The solvent is distilled-off in vacuum at the temperature of not more than 50° C. to dryness. The resulting residue is dissolved in benzene, placed into a column packed with silica gel and eluted with a mixture of benzene-ethylacetate (6:1).

Collected are fractions containing 11-desoxy-17α-hydroxy-21-[p-di(2-chloroethyl)aminophenylacetate] corticosterone with $R_f$ about 0.50 in the system benzene-ethylacetate (3:2) on Silufol UV$_{254}$ plates.

The solvent is distilled-off in vacuum and the final product (I) is crystallized from ether, the yield 17.99 g (51.54%).

Calculated, %: C 65.55; H 7.16; Cl 11.73. $C_{33}H_{43}Cl_2NO_5$. Found, %: C 65.44; H 7.12; Cl 11.56.

UV-spectrum (in ethanol): $\lambda_{max}$. 256 nm;

IR-spectrum: $\nu_{C=O}$ 1,742 cm$^{-1}$; 1,723 cm$^{-1}$; 1,653 cm$^{-1}$; $\nu_{C=Cl}$ 744 cm$^{-1}$, 686 cm$^{-1}$, 655 cm$^{-1}$.

EXAMPLE 2

Preparation of 11-desoxy-17α-hydroxy-21-[p-di(2-chloroethyl)aminophenylbutyrate] corticosterone (II)

The preparation of compound II is effected in a manner similar to the synthesis of the compound described in Example 1 hereinabove.

Entered into the reaction of acylation are 11-desoxy-17α-hydroxycorticosterone and mixed anhydride of p-di(2-chloroethyl)aminophenylbutyric acid and isovaleric acid. The reaction mixture is stirred at the temperature of 80° C. for 4 hours. The following operations are carried out as described in the foregoing Example 1. The product is chromatographed in a column with silica gel, eluted with a mixture benzene-ethylacetate (6:1). The yield of compound II is 40% as calculated for the starting hormone.

Found, %: C 66.85; H 7.59; Cl 11.19. $C_{33}H_{47}Cl_2NO_5$. Calculated %: C 66.43; H 7.48; Cl 11.22.

Industrial Applicability

The derivatives of 11-desoxy-17α-hydroxycorticosterone are useful in medicine for the treatment of cancer and for transplantation of organs and tissues.

We claim:

1. 11-Desoxy-17α-hydroxycorticosterone derivatives of the general formula:

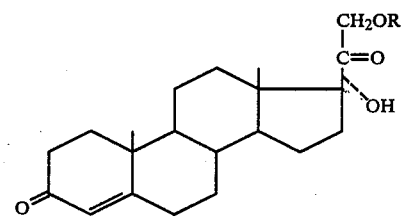

wherein R is —CO(CH$_2$)$_n$C$_6$H$_4$N(CH$_2$CH$_2$Cl)$_2$ in which n=1.

2. A pharmaceutical composition useful for the treatment of tumors and as an immunodepressant, comprised of an effective amount of the derivative of claim 1 and a pharmaceutically acceptable carrier.

3. A method for treating a tumor in a subject in need of such treatment which comprises administering to said subject an anti-tumor effective amount of the composition of claim 2.

4. A method of producing an immunodepressant effective in a subject in need of such treatment, which comprises administering to said subject an immunodepressing amount of the composition of claim 2.

* * * * *